United States Patent [19]

Marburg et al.

[11] 4,292,427

[45] Sep. 29, 1981

[54] CEPHALOSPORIN COMPOUNDS

[75] Inventors: Stephen Marburg, Plainfield; Janos Kollonitsch, Westfield, both of N.J.

[73] Assignee: Merck & Co., Inc., Rahway, N.J.

[21] Appl. No.: 103,123

[22] Filed: Dec. 13, 1979

Related U.S. Application Data

[60] Division of Ser. No. 742,486, Nov. 17, 1976, which is a continuation of Ser. No. 647,961, Jan. 9, 1976, abandoned, which is a continuation of Ser. No. 487,851, Jul. 11, 1974, abandoned, which is a continuation of Ser. No. 275,614, Jul. 27, 1972, abandoned, which is a continuation-in-part of Ser. No. 174,949, Aug. 25, 1971, abandoned.

[51] Int. Cl.$^3$ .............................................. C07D 501/20

[52] U.S. Cl. ..................................... 544/021; 424/246; 544/16; 544/22

[58] Field of Search ............................ 544/16, 20, 21; 424/246

[56] References Cited

U.S. PATENT DOCUMENTS 3,355,452  11/1967  Urech et al. ........................ 260/243
3,726,865  4/1973  Bickel et al. ........................ 544/16

*Primary Examiner*—Nicholas S. Rizzo
*Attorney, Agent, or Firm*—James A. Arno; Hesna J. Pfeiffer

[57] ABSTRACT

Alcohols are reacted with certain isocyanate compounds to produce the N-substituted carbamoyloxy derivatives which are cleaved to obtain the carbamate.

1 Claim, No Drawings

CEPHALOSPORIN COMPOUNDS

This is a division of application Ser. No. 742,486, filed Nov. 17, 1976; which in turn is a continuation of U.S. patent application Ser. No. 647,961 filed Jan. 9, 1976, now abandoned; which in turn is a continuation application of U.S. Ser. No. 487,851 filed July 11, 1974; now abandoned, which in turn is a continuation of U.S. Ser. No. 275,614, filed July 27, 1972; now abandoned, which in turn is a continuation-in-part of U.S. Ser. No. 174,949, filed Aug. 25, 1971, now abandoned.

This invention relates to the preparation of carbamates and products useful in their preparation. More particularly, it is concerned with a method of converting alcohols to the corresponding carbamoyloxy derivatives, reagents suitable for this conversion, and with intermediate substituted carbamoyloxy compounds useful in their preparation.

The carbamates are valuable derivatives of alcohols which are useful in their identification and characterization. In addition, carbamates such as meprobamate, carbachol, and novobiocin have been found to be useful medicinal products. More recently it has been found that 3-carbamoyloxymethylcephalosporins obtained by fermentation are valuable antibiotic substances. The process of the present invention is particularly valuable in providing a method suitable for the preparation of such cephalosporins as well as other carbamates.

In accordance with one embodiment of this invention, it is now found that alcohols can be converted to the corresponding carbamoyloxy compounds by reacting the alcohol with an isocyanate compound of the general formula $R_1NCO$ where $R_1$ represents a labile group which is readily replaced by hydrogen to produce the corresponding substituted carbamate and then replacing the labile group with hydrogen. This process can be illustrated as follows:

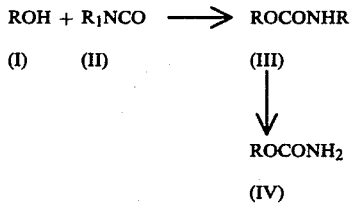

The group represented by $R_1$ is a labile group which is readily cleaved and replaced by hydrogen. Thus, $R_1$ can be a hydrocarbyl group or substituted hydrocarbyl group such as benzhydryl or a substituted benzhydryl group, a carboxylic acid acyl group such as trifluoroacetyl, or a hydrocarbyloxycarbonyl or substituted hydrocarbyloxycarbonyl group. By the term substituted hydrocarbyl is meant a hydrocarbyl group wherein one or more of the hydrogen atoms is replaced by halo or an organic radical such as alkoxy, alkyl, and the like.

In this process the alcohol I, wherein R represents the organic radical of the alcohol, is reacted with the substituted isocyanate II, wherein $R_1$ represents a labile group, to produce the N-substituted intermediate product III, which is treated with a reagent capable of replacing $R_1$ with hydrogen to produce the desired carbamate IV. In carrying out this process, we prefer to use a substituted isocyanate having an $R_2$-oxy carbonyl group of the formula $R_2OCONCO$ wherein $R_2$ is a hydrocarbyl or substituted hydrocarbyl group which is labile and can be readily removed to form the desired carbamate. Thus, $R_2$ can be an alkyl group, a substituted alkyl group such as a haloalkyl, an aralkyl group, or a substituted aralkyl group. Isocyanates which are particularly useful in carrying out our invention that might be mentioned are 2,2,2-trichloro (or tribromo)ethoxycarbonyl, benzyloxycarbonyl, benzhydryloxycarbonyl, t-butyloxycarbonyl, p-methoxybenzyloxycarbonyl, benzoylmethoxycarbonyl, trifluoroacetyl and o-nitrobenzyloxycarbonyl. These represent preferred reactants since the N-substituted carbamates obtained can be readily cleaved and replaced by hydrogen to obtain the desired carbamate. Thus, the 2,2,2-trihaloethoxycarbonyl group and the benzoylmethoxycarbonyl group are readily removed by reaction with zinc in the presence of an acid such as acetic or formic acid; the benzyloxycarbonyl group is removed by reaction with hydrogen in the presence of a noble metal catalyst such as palladium catalyst, the t-butyloxycarbonyl group, the benzhydryloxycarbonyl group, and the p-methoxybenzyl group are readily removed by reaction with trifluoroacetic acid and anisole, the trifluoroacetyl group is readily removed by hydrolysis, and the o-nitrobenzyloxycarbonyl group is readily removed by UV irradiation.

Alternatively, and in accordance with a further embodiment of our invention, a hydrocarbyl isocyanate such as an aralkyl isocyanate, for example benzhydryl isocyanate, is reacted to form the N-benzhydryl carbamoyloxy compound. The benzhydryl substituent can then be cleaved, preferably with acid reagents.

The first step of the above-described process, namely, the preparation of the intermediate imidodicarboxylates or the N-hydrocarbyl carbamoyloxy compound (III) is carried out by intimately contacting the alcohol with the isocyanate, preferably in a non-protic solvent such as methylene chloride, tetrahydrofuran, dimethylformamide, and the like. In general, we prefer to carry out the reaction under anhydrous conditions and to have an excess of the isocyanate present in order to obtain maximum yields of the desired intermediate product. In general, the reaction can be carried out at temperatures between about 0° C. and 100° C. However, it is generally preferred to carry out the initial addition of the isocyanate at a low temperature since the reaction appears to be exothermic. The precise conditions for carrying out this process will depend in part upon the particular alcohol which is being reacted. The removal of the protecting group and its replacement by hydrogen is readily carried out by procedures mentioned above.

The process of this invention is valuable for producing cephalosporin compounds having a 3-carbamoyloxymethyl substituent. This embodiment of our invention can be represented as follows:

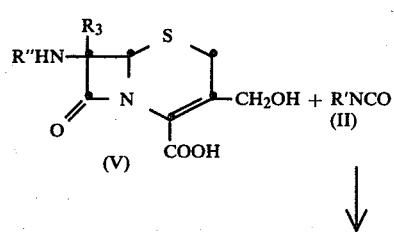

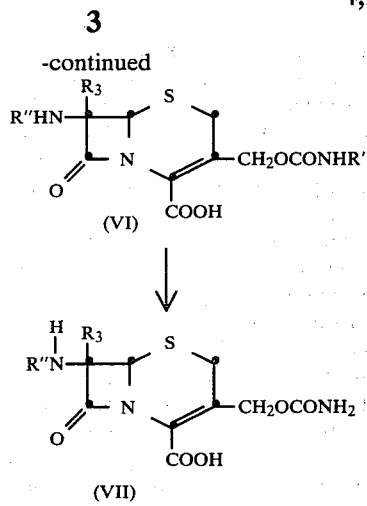

wherein R' is as defined above, R'' represents hydrogen or an acyl radical and $R_3$ represents hydrogen or a group such as methoxy. In this process the 3-hydroxymethylcephalosporin compound (V) is reacted with the isocyanate (II) to produce the intermediate N-substituted carbamoyloxy compound (VI) which is then deblocked to produce the 3-carbamoyloxymethyl compound. The acyl radical represented by R'' can be an acyl group of a carboxylic acid or a substituted sulfonyl radical such as phenylsulfonyl, ethylsulfonyl, benzylsulfonyl, 2,5-dimethylphenylsulfonyl, 4-chlorophenylsulfonyl, 4-methoxyphenylsulfonyl, and the like. Thus, R'' can be an aliphatic, aromatic or heterocyclic, araliphatic or heterocyclylaliphatic carboxylic acid radical such as the acyl radical of the known cephalosporins and penicillins. The acyl substituents of the general formula $R_{11}R_{10}CHCO$ wherein $R_{10}$ and $R_{11}$ are as defined below represent a preferred group of substituents because of their generally useful antibiotic activity. $R_{10}$ represents hydrogen, halo, amino, guanidino, phosphono, hydroxy, tetrazolyl, carboxy, sulfo or sulfamino. $R_{11}$ represents phenyl, substituted phenyl, a monocyclic heterocyclic 5- or 6-membered ring containing one or more oxygen, sulfur or nitrogen atoms in the ring, substituted heterocycles, phenylthio, heterocyclic or substituted heterocyclic thio groups; or cyano. The substituents can be halo, carboxymethyl, guanidino, guanidinomethyl, carboxamidomethyl, aminomethyl, nitro, methoxy or methyl. Examples of these preferred substituents that might be mentioned are phenacetyl, 3-bromophenylacetyl, p-aminomethylphenylacetyl, 4-carboxylmethylphenylacetyl, 4-carboxamidomethylphenylacetyl, 2-furylacetyl, 5-nitrofurylacetyl, 3-furylacetyl, 2-thienylacetyl, 5-chlorothienylacetyl, 5-methoxythienylacetyl, α-guanidino-2-thienylacetyl, 3-thienylacetyl, 4-methylthienylacetyl, 3-isothiazolylacetyl, 4-methoxyisothiazolylacetyl, 4-isothiazolylacetyl, 3-methylisothiazolylacetyl, 5-isothiazolylacetyl, 3-chloroisothiazolylacetyl, 3-methyl-1,2,5-oxadiazolylacetyl, 1,2,5-thiadiazolyl-4-acetyl, 3-methyl-1,2,5-thiadiazolyl-4-acetyl, 3-chloro-1,2,5-thiadiazolyl-4-acetyl, 3-methoxy-1,2,5-thiadiazolyl-4-acetyl, phenylthioacetyl, 4-pyridylthioacetyl, cyanoacetyl, tetrazolylacetyl, α-fluorophenylacetyl, D-phenylglycyl, 3-hydroxy-D-phenylglycyl, 2-thienylglycyl, 3-thienylglycyl, phenylmalonyl, 3-chlorophenylmalonyl, 2-thienylmalonyl, 3-thienylmalonyl, α-phosphonophenylacetyl, α-sulfaminophenylacetyl, α-hydroxyphenylacetyl, α-tetrazolylphenylacetyl and α-sulfophenylacetyl.

Particularly preferred 3-hydroxymethylcephalosporin compounds which can be converted to the corresponding 3-carbamoyloxymethylcephalosporin compounds in accordance with this invention are those wherein $R_{10}$ is hydrogen, amino, or carboxy and $R_{11}$ is phenyl or a 5-membered heterocyclic ring having one oxygen or one sulfur hetero atom, and especially those wherein R'' is benzylcarbonyl, 2- and 3-thienylmethylcarbonyl or 2- and 3-furylmethylcarbonyl.

The cephalosporin carbamates are prepared by reacting cephalosporin compounds having a 3-hydroxymethyl substituent, or a salt or ester of such cephalosporins, with the isocyanate and then cleaving the resulting reaction product as described above. If the cephalosporin being reacted contains other substituents which react with the isocyanate, such as other hydroxy groups or amino groups, these substituents are blocked or protected by groups such as trityl, tertiary butyloxycarbonyl, N-trichloroethoxycarbonyl, and the like, and then removed after the carbamoyloxy group is introduced. For example, 7-tritylaminocephalosporanic acid is intimately contacted with citrus acetylesterase to produce 7-tritylaminodesacetylcephalosporanic acid which, on reaction with the isocyanate and hydrolysis of the reaction product, affords the 3-carbamoyloxymethyl compound. Removal of the protective trityl group by methods known in the art affords 3-carbamoyloxymethyl-7-aminodesacetylcephalosporanic acid which can be acylated by known methods to produce 3-carbamoyloxymethyldesacetylcephalosporins.

Alternatively, 3-hydroxymethyl-7-acylamido-3-cephem-4-carboxylic acid and the corresponding compounds having a substituent at the 7-position, such as methoxy, in place of hydrogen, can be converted to the corresponding 3-carbamoyloxymethylcephalosporin compounds by the process of this invention.

The 3-carbamoyloxymethylcephalosporins prepared in accordance with the process of this invention are valuable antibiotics which are active at low levels against various gram-positive and gram-negative pathogens such as *Staphylococcus aureus, Staphylococcus pyogenes, Proteus vulgaris, Escherichia coli* and the like. These new cephalosporins are therefore useful in treating infections in humans and animals. They can also be used in dilute aqueous concentrations containing less than 100 parts of antibiotic per million parts of solution in removing susceptible organisms from pharmaceutical, medical and dental equipment, and for isolating microorganisms from mixtures of microorganisms.

Pursuant to a further embodiment of the present invention, it is found that the isocyanates used in the process of our invention are prepared by reacting the corresponding carbamate with oxalyl chloride, preferably in a non-protic solvent such as ethylene dichloride. Thus, the isocyanates are prepared by slowly adding to a cooled (about 0° C.) 1-2 molar solution of the carbamate in ethylene dichloride a 1.5 molar oxalyl chloride solution in ethylene dichloride; 1.5 to 2 molar equivalents of oxalyl chloride being required. After the addition of the oxalyl chloride is complete, the solution is refluxed for 10-20 hours, after which the solvent is evaporated and the isocyanate isolated by vacuum distillation.

The benzyl, t-butyl and p-methoxybenzyl carbamates can be prepared by processes known in the art. The 2,2,2-trihaloethyl carbamates are prepared by reacting the trihaloethoxycarbonyl chloride with ammonia in an aqueous medium at a pH of about 9.8 The benzhydryl carbamate is conveniently prepared by reacting benzhydrol with 2,2,2-trichloroethoxycarbonyl isocyanate and treating the resulting imidocarboxylate with zinc-copper couple in the presence of acetic acid.

The following examples are provided to illustrate the above-described processes of the present invention.

EXAMPLE 1

Preparation of 2,2,2-trichloroethoxycarbonyl isocyanate

A. Preparation of 2,2,2-trichloroethyl carbamate

Into a mixture of 17 ml. of concentrated aqueous $NH_3$ and 17 ml. of water there is added under stirring and cooling in an ice bath 10 ml. of 2,2,2-trichloroethoxycarbonyl chloride in 1–2 ml. portions at such a rate as to keep the temperature below 20° C. A white precipitate forms and an additional 4 ml. concentrated ammonia is added to keep the pH at about 9.8. After completion of the addition, stirring is continued for 1 hour after which time the precipitate is collected on a filter, dried by dissolving in methylene chloride and treating with anhydrous magnesium sulfate. Concentration affords 12.9 g. of 2,2,2-trichloroethyl carbamate. Recrystallization from cyclohexane affords an analytical sample (needles) m.p. 62°–64° C.

B. Preparation of 2,2,2-trichloroethoxycarbonyl isocyanate 2,2,2-Trichloroethyl carbamate (25.1 g., 131 mmoles) is dissolved in 100 ml. of dry ethylene dichloride, cooled to 10° C. and 15.5 ml. oxalyl chloride in 100 ml. ethylene dichloride is added. The solution is allowed to warm to room temperature and then refluxed for 16 hours. A solid is deposited. Then 185 ml. ethylene dichloride is distilled off and the remainder filtered and distilled in vacuo. The fraction distilling at 60°–69° C./7–9 mm. is collected, affording 12.38 g. of trichloroethoxycarbonyl isocyanate, (D=1.6) as a mobile, extremely moisture sensitive liquid [IR $(CCl_4)$:4.55$\mu$ (N=C=O), twin carbonyl at 5.62$\mu$, 5.70$\mu$]. The material appears to be indefinitely stable when kept dry and in the refrigerator.

Following the procedures of this example and using 2,2,2-tribromoethoxycarbonyl chloride as the starting material in place of the trichloro compound, 2,2,2-tribromoethoxycarbonyl isocyanate is obtained.

EXAMPLE 2

Preparation of benzyloxycarbonyl isocyanate, t-butyloxycarbonyl isocyanate, benzhydryloxycarbonyl isocyanate, p-methoxybenzyloxycarbonyl isocyanate, benzoylmethoxycarbonyl isocyanate and o-nitrobenzyloxycarbonyl isocyanate Following the procedures described in Example 1B and using a molar equivalent amount of benzyl carbamate, t-butyl carbamate, benzhydryl carbamate, p-methoxybenzyl carbamate, 2-hydroxyacetophenone carbamic acid ester ($C_6H_5COCH_2OCONH_2$) or o-nitrobenzyl carbamate in place of the 2,2,2-trichloromethyl carbamate, the corresponding isocyanates listed in the above title are obtained.

The benzyl carbamate, the t-butyl carbamate and the p-methoxybenzyl carbamate are known compounds which can be prepared by processes known in the art. The benzyl carbamate can also be prepared as described in Example 3.

The 2-hydroxyacetophenone carbamic acid ester is prepared as follows:

13.6 g. of 2-hydroxyacetophenone is dissolved in 200 ml. of dry methylene chloride and this solution charged to a flask containing 13.0 g. sodium cyanate. The mixture is slowly stirred and 16 ml. trifluoroacetic acid is added at such a rate that the temperature is maintained below 50° C. After completion of the addition, stirring is continued for 2 hours and then the solution is washed with water and dried. Concentration of the organic solution affords the product, 2-hydroxyacetophenone carbamic acid ester.

The benzhydryl carbamate is prepared as follows:

To 368 mg. of benzhydrol (diphenylmethanol) dissolved in 4 ml. of tetrahydrofuran and cooled in an ice bath is added in a dropwise manner 0.3 ml. of trichloroethoxycarbonyl isocyanate. The solution is warmed to and kept at room temperature for 18 hours. It is then concentrated in vacuo to an oil which crystallizes on trituration with hexane, affording 720 mg. of benzhydryl 2,2,2-trichloroethyl imidodicarboxylate IR($CHCl_3$): 2.92, 5.50; 5.70$\mu$; m.p. 142°–143° C.

225 mg. benzhydryl 2,2,2-trichloroethyl imidodicarboxylate is dissolved in 4 ml. of glacial acetic acid and stirred at room temperature with 400 mg. of zinc-copper couple and 600 mg. of a non-aqueous cation exchanger for 4 hours. The solution is then filtered and concentrated to afford the desired product, benzhydryl carbamate, m.p. 123° C.

The o-nitrobenzyl carbamate is prepared as follows:

15.3 g. (0.1 mole) of o-nitrobenzyl alcohol is dissolved in 200 ml. of chloroform in a glass bomb tube. The tube is cooled in an ice bath and phosgene is introduced until 20 g. has been condensed. The tube is sealed and heated at 65° C. for 4 hours. The solvent and excess reagent are then removed by distillation and the product, o-nitrobenzyl chloroformate, is obtained as a yellow oil.

The above yellow oil is added in small portions to a cooled stirred concentrated aqueous ammonia solution at such a rate as to keep the temperature below 15° C. Enough ammonia is used so that the pH does not fall below 9. The white solid which is deposited is dissolved in chloroform and the resultant solution is washed with water and dried over sodium sulfate. Concentration and crystallization from benzene-cyclohexane affords the o-nitrobenzyl carbamate.

EXAMPLE 3

Preparation of benzyl carbamate

A. Preparation of benzyl 2,2,2-trichloroethyl imidodicarboxylate

Benzyl carbamate is prepared by dissolving 354 mg. (3.28 mmoles) benzyl alcohol in 3 ml. methylene chloride in a 2-neck 10 ml. flask fitted with a condenser topped with a drying tube and serum cap. The solution is cooled in an ice bath and 0.48 ml. (770 mg., 3.5 mmoles) of trichloroethoxycarbonyl isocyanate is introduced with a syringe through the serum cap. An exotherm is noted. After stirring at room temperature for 40 minutes, the solution is concentrated to an oil and recrystallized from cyclohexane to yield 980 mg. of benzyl 2,2,2-trichloroethyl imidodicarboxylate, m.p. 88.5°–89.5° C. An analytical sample has a m.p. 89.5°–90.5° C.

B. Preparation of benzyl carbamate 300 mg. of activated zinc is covered with 5 ml. of 90% aqueous acetic acid. 200 mg. of benzyl 2,2,2-trichloroethyl imidodicarboxylate is added and the mixture stirred for 2.5 hours. The zinc is then filtered off and the filtrate saturated with $H_2S$. The precipitated zinc sulfide is separated by centrifugation and washed with 90% aqueous acetic acid. The combined acetic acid solutions are concentrated in vacuo, the residue triturated with cyclohexane to afford 97 mg. of a crystalline material whose IR spectrum is identical with that of authentic benzyl carbamate.

EXAMPLE 4

Preparation of phenyl carbamate via phenyl trichloroethoxycarbonyl imidodicarboxylate

A. Preparation of the imidodicarboxylate

To a solution of 87 mg. (0.925 mmole) of phenol in 2 ml. of dichloromethane there is added 0.150 ml. (1.1 mmole) of 2,2,2-trichloroethoxycarbonyl isocyanate. After stirring overnight the solvent is evaporated to give a white solid; after recrystallization from ethanol-water (1:1), phenyl 2,2,2-trichloroethoxycarbonyl imidodicarboxylate is obtained in 80% yield, m.p. 143°–144° C.

B. Preparation of phenyl carbamate 0.599 g. of the imidodicarboxylate obtained in A above is dissolved in 25 ml. of 90% acetic acid; 0.4 g. of zinc dust is added and the mixture is stirred overnight at room temperature. It is filtered, concentrated in vacuo to give crude phenyl carbamate. Recrystallization from water gives pure phenyl carbamate, m.p. 147°–148° C. Infrared spectrum (in acetonitrile) is identical with that of an authentic sample.

EXAMPLE 5

Preparation of 3-carbamoyloxymethyl-7-(2-thienylacetamido)-3-cephem-4-carboxylic acid

A. Preparation of 3-[N-(2,2,2-trichloroethoxycarbonyl)carbamoyloxymethyl]-7-(2-thienylacetamido)-3-cephem-4-carboxylic acid 641 mg. (1.62 mmoles) of 3-hydroxymethyl-7-(2-thienylacetamido)-3-cephem-4-carboxylic acid potassium salt is dissolved in 25 ml. of 0.05 M phosphate buffer and is covered with 25 ml. ethyl acetate. The mixture is stirred and cooled in an ice bath and the pH adjusted to 2.2 with about 1.4 ml. of 2.5 N HCl. The ethyl acetate is separated and the aqueous layer washed twice with 25 ml. cold ethyl acetate. The combined organic layers are washed with saturated sodium chloride solution, dried over anhydrous sodium sulfate and concentrated to yield 488 mg. of the free acid.

This material, in a round bottom flask fitted with a drying tube and magnetic stirrer, is covered with 10 ml. (dry) methylene chloride, cooled in an ice bath and 0.205 ml. 2,2,2-trichloroethoxycarbonyl isocyanate added with a syringe. Then 4 ml. dry tetrahydrofuran is added, and after warming to room temperature the solid rapidly goes into solution. After stirring at room temperature for 1 hour, the solution is concentrated to dryness to afford 927 mg. of crude product. A crystallization from methanol-water followed by a methanol-ether-cyclohexane recrystallization affords 600 mg. of 3-[N-(2,2,2-trichloroethoxycarbonyl)carbamoyloxymethyl]-7-(2-thienylacetamido)-3-cephem-4-carboxylic acid, m.p. 114°–116° C.

The product is soluble in aqueous $NaHCO_3$ solution and precipitated with diluted HCl. The infrared spectrum (Nujol) shows NH at 2.87 and 3.05μ; CO (lactam) at 5.56μ; imido diester and acid CO at 5.75 and a shoulder at 5.85μ; and amide at 5.98μ.

B. Preparation of 3-carbamoyloxymethyl-7-(2-thienylacetamido)-3-cephem-4-carboxylic acid 10 g. of a non-aqueous cation exchange resin (Amberlyst 15) is covered with 50 ml. of glacial acetic acid in a flask fitted with a drying tube and magnetic stirrer. To this is added 4.1 g. (50 mmoles) of anhydrous sodium acetate (which dissolves) and 850 mg. (1.485 mmole) of 3-[N-(2,2,2-trichloroethoxycarbonyl)carbamoyloxymethyl]-7-(2-thienylacetamido)-3-cephem-4-carboxylic acid. A yellow solution results. 2.6 g. of activated zinc dust is added and the mixture stirred for 4 hours at room temperature. After filtration through diatomaceous earth and washing the residue with 50 ml. of acetic acid, the combined filtrates are concentrated to a sludge in vacuo and triturated with 100 ml. of ether. The non-soluble residue is dissolved in 35 ml. of water and 35 ml. of ethyl acetate and the pH adjusted to 2.0 with 7.5 ml. of 2.5 N HCl. The ethyl acetate layer is separated and the aqueous layer extracted with 30 ml. of ethyl acetate. The combined organic layers are washed with saturated sodium chloride solution, dried over sodium sulfate and concentrated in vacuo to give 400 mg. crude product. Crystallization from isopropanol affords 125 mg. of a white crystalline solid whose IR shows NH at 2.92, 3.05μ; lactam at 5.63μ; carbamate at 5.85μ and amide at 6.03μ. The NMR, in addition to the peaks listed below, shows about 0.8 mole isopropanol.

| No. of H | Chem Shift (ppm) | Multiplicity | (Hz) | Assignment |
|---|---|---|---|---|
| 2 | 3.51, 3.55 | split peak | — | C-2 methylene |
| 2 | 3.77 | singlet | — | thienylacetyl methylene |
| 2 | 4.77 | AB doublet | 13 | C-3 exocyclic methylene |
| 1 | 5.21 | doublet | 4.5 | C-6-H |
| 1 | 5.68 | double doublet | 8, 4.2 | C-7-H |
| 1.7 | 6.57 | broad singlet | — | $NH_2$ |
| 2 | 6.95 | mult | — | thienyl |
| 1 | 7.37 | mult | — | thienyl |
| 1 | 9.07 | doublet | 8 | NH |

The potassium 3-hydroxymethyl-7-(2-thienylacetamido)-3-cephem-4-carboxylate used as the starting material in this example is prepared by incubating the known sodium 7-(2-thienylacetamido)-cephalosporanate with citrus esterase in accordance with procedures well known in this art.

EXAMPLE 6

When the process of Example 5A is carried out using an equivalent amount of benzyloxycarbonyl isocyanate, t-butyloxycarbonyl isocyanate, benzhydryloxycarbonyl isocyanate, p-methoxybenzyloxycarbonyl isocyanate, or benzoylmethoxycarbonyl isocyanate in place of the 2,2,2-trichloroethoxycarbonyl isocyanate, the corresponding substituted carbamoyl cephalosporin compound of the formula

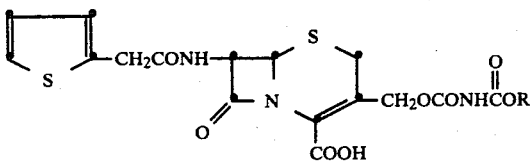

wherein
R is C$_6$H$_5$CH$_2$—(CH$_3$)C—(C$_6$H$_5$)$_2$CH—p-CH$_3$OC$_6$H$_4$CH$_2$—C$_6$H$_5$COCH$_2$-, respectively, is obtained.

EXAMPLE 7

The 3-[N-(benzyloxycarbonyl)carbamoyloxymethyl]-7-(2-thienylacetamido)-3-cephem-4-carboxylic acid obtained as described in Example 6 is dissolved in 5 to 15 volumes of alcohol and 10 to 200% by weight of palladium catalyst is added. The mixture is shaken with hydrogen at pressures ranging from 1 atmosphere to 150 atmospheres, but preferably at 3 atmospheres, from 15 minutes to 16 hours at room temperature. After completion of the hydrogen uptake, the reaction mixture is freed of catalyst by filtration and concentrated in vacuum to afford 3-carbamoyloxymethyl-7-(2-thienylacetamido)-3-cephem-4-carboxylic acid.

EXAMPLE 8

The 3-[N-(t-butyloxycarbonyl)carbamoyloxymethyl]-7-(2-thienylacetamido)-3-cephem-4-carboxylic acid (600 mg.) prepared as described in Example 6 is dissolved in 1 ml. of anisole and cooled to 0° C. To this solution is added 5 ml. of trifluoroacetic acid, and the resulting reaction mixture is maintained at 0°-5° C. for 5 minutes. The trifluoroacetic acid is then removed in high vacuum (<0.1 mm. Hg) and when all the acid is removed 1 ml. of anisole is added, and the mixture is heated to 30° C. under reduced pressure until all the volatile products are removed. The residue is then dissolved in a small amount of aqueous sodium bicarbonate solution and extracted with ethyl acetate. The extracted aqueous solution is acidified with phosphoric acid to pH 2.5 and the product is extracted into ethyl acetate. The organic solution is dried over anhydrous sodium sulfate and the dried solution is evaporated to afford 3-carbamoyloxymethyl-7-(2-thienylacetamido)-3-cephem-4-carboxylic acid.

EXAMPLE 9

When 3-[N-(benzhydryloxycarbonyl)carbamoyloxymethyl]-7-(2-thienylacetamido)-3-cephem-4-carboxylic acid or 3-[N-(p-methoxybenzyloxycarbonyl)carbamoyloxymethyl]-7-(2-thienylacetamido)-3-cephem-4-carboxylic acid prepared as described in Example 6 are cleaved by reaction with trifluoroacetic acid and anisole following the procedures described in Example 8, 3-carbamoyloxymethyl-7-(2-thienylacetamido)-3-cephem-4-carboxylic acid is obtained.

EXAMPLE 10

The 3-[N-(benzoylmethoxycarbonyl)carbamoyloxymethyl]-7-(2-thienylacetamido)-3-cephem-4-carboxylic acid prepared as described in Example 6 is dissolved in glacial acetic acid and a 10-fold molar excess of activated zinc dust is added. The resultant mixture is stirred at room temperature for 2.5 hours, after which the excess zinc is filtered off and washed with glacial acetic acid. The combined acetic acid fractions are concentrated in vacuo and the residue is taken up in water and ethyl acetate and treated with H$_2$S for 15 minutes. Filtration through diatomaceous earth removes the zinc sulfide. The pH of the filtrate is adjusted to 2.5 with phosphoric acid, and the ethyl acetate layer is separated and the aqueous solution is extracted with more ethyl acetate. The ethyl acetate layer is then layered with water made basic to pH 6.0 with potassium hydroxide and the aqueous layer is separated. The aqueous layer is then reacidified with phosphoric acid to pH 2.5 and extracted with ethyl acetate. The organic layer is dried and concentrated to afford the desired product, 3-carbamoyloxymethyl-7-(2-thienylacetamido)-3-cephem-4-carboxylic acid.

EXAMPLE 11

Preparation of 3-carbamoyloxymethyl-7-amino-3-cephem-4-carboxylic acid

A. Preparation of 7-(t-butoxycarbonyl)aminocephalosporanic acid 27.2 g. (0.1 mole) of 7-aminocephalosporanic acid is dissolved in 250 ml. of water and the pH of the solution is adjusted to 8.7 with 15% sodium hydroxide. To this solution is added 16 g. (0.11 mole) of t-butyloxycarbonyl azide dropwise with rapid stirring over 1 hour, while maintaining the pH of the solution at 8.7 with the use of a pH stat.

The end of the reaction is indicated by the reaction mixture maintaining itself at a constant pH of 8.7. The pH of the solution is adjusted to 2 with phosphoric acid and extracted into ethyl acetate (3×500 ml.). The ethyl acetate extract is washed twice with water, dried and evaporated to give 7-(t-butoxycarbonyl)aminocephalosporanic acid.

B. Preparation of potassium 3-hydroxymethyl-7-[N-(t-butoxycarbonyl)amino]-3-cephem-4-carboxylate 7-(t-Butoxycarbonyl)aminocephalosporanic acid (18.5 g.) is dissolved in 1000 ml. of a preparation containing citrus acetylesterase, the temperature is maintained at 30° C. and the pH is maintained between 6.5–6.8 by addition of 1 N NaOH. After the pH of the reaction mixture maintains itself, the reaction mixture is stirred a further 2 hours and then acidified to pH 2 and extracted with 3×500 ml. portions of ethyl acetate. The ethyl acetate extract is washed twice with water and then extracted with water containing enough potassium bicarbonate to maintain the pH at 7.5. The aqueous phase is freeze dried and the residue is crystallized from methanol/isopropanol to give potassium 3-hydroxymethyl-7-[N-(t-butoxycarbonyl)amino]-3-cephem-4-carboxylate.

C. Preparation of 3-carbamoyloxymethyl-7-[N-(t-butoxycarbonyl)amino]-3-cephem-4-carboxylic acid 5 g. of potassium 3-hydroxymethyl-7-[N-(t-butoxycarbonyl)amino]-3-cephem-4-carboxylate is reacted with 2,2,2-trichloroethoxycarbonyl isocyanate and the resulting product is deblocked following the procedures described in Example 5 to afford 3-carbamoyloxymethyl-7-[N-(t-butoxycarbonyl)amino]-3-cephem-4-carboxylic acid.

D. Preparation of 3-carbamoyloxymethyl-7-amino-3-cephem-4-carboxylic acid 1.5 g. of the t-butoxycarbonyl derivative of C above in 15 ml. anisole and 25 ml. of trifluoroacetic acid are stirred at 0° C. for 10 minutes. The resulting reaction mixture is evaporated at 0.1 mm. at 30° C. Anisole (5 ml.) is added and evaporated under 0.1 mm. at 30° C. The residue is taken up in water (20 ml.) and adjusted to pH 7.5 by the addition of 0.1 N NaOH. The aqueous solution is extracted with 3 × 10 ml. of $CH_2Cl_2$ and then adjusted to pH 2.5 with careful addition of a strongly acidic cation exchange resin of the sulfonate type having a styrene-divinylbenzene matrix (Dowex 50) ($H^+$ cycle). The solid resin is filtered off and the filtrate is freeze dried to give 3-carbamoyloxymethyl-7-amino-3-cephem-4-carboxylic acid. This product can be converted to 7-acylamido derivatives such as the 7-(D-α-aminophenylacetamido)cephalosporin in accordance with methods known in the art.

EXAMPLE 12

When 3-hydroxymethyl-7-methoxy-7-(2-thienylacetamido)-3-cephem-4-carboxylic acid is reacted with 2,2,2-trichloroethoxycarbonyl isocyanate and the resulting imidodicarboxylate is deblocked following the procedures described in Example 5, 3-carbamoyloxymethyl-7-methoxy-7-(2-thienylacetamido)-3-cephem-4-carboxylic acid is obtained.

The starting material of this example is prepared by treating sodium 7-methoxy-7-(2-thienylacetamido)-cephalosporanate with citrus esterase following the procedures described in Example 12B above.

The sodium 7-methoxy-7-(2-thienylacetamido)-cephalosporanate is prepared as described in the pending U.S. application of Christensen et al. U.S. Ser. No. 149,364 filed June 2, 1971.

EXAMPLE 13

Trifluoroacetyl isocyanate (prepared as described in the art) is dissolved in dry tetrahydrofuran at −10° C. and added to a solution of 3-hydroxymethyl-7-(2-furylacetamido)-3-cephem-4-carboxylic acid at −10° C., and the mixture is allowed to warm very slowly to room temperature. After stirring 1 hour at room temperature, the solvent is removed in vacuo and the product, 3-[N-(trifluoroacetyl)carbamoyloxymethyl]-7-(2-furylacetamido)-3-cephem-4-carboxylic acid, is obtained.

This is dissolved in a 2 molar sodium acetate-acetic acid buffer, the pH of which can vary from 4 to 6, and the solution is stirred from 10 to 72 hours at room temperature. Then the solution is acidified to pH 2.5 with phosphoric acid and extracted with ethyl acetate. The organic solution is then thoroughly washed with water, dried over sodium sulfate and concentrated to afford the desired product, 3-carbamoyloxymethyl-7-(2-furylacetamido)-3-cephem-4-carboxylic acid.

The starting material of this example is prepared by treating sodium 7-methoxy-7-(2-furylacetamido)cephalosporanate with citrus esterase following the procedures described in Example 12B above. The sodium 7-methoxy-7-(2-furylacetamido)cephalosporanate is prepared as described in the pending U.S. application of Christensen et al., U.S. Ser. No. 149,364 filed June 2, 1971.

EXAMPLE 14

510 mg. (1.58 mmoles) of 3-hydroxymethyl-7-(2-phenylacetamido)-3-cephem-4-carboxylic acid, prepared from the potassium salt as in Example 5, is dissolved in 4 ml. of dry tetrahydrofuran and cooled in an ice bath. To the stirred mixture is added 355 mg. (1.70 mmoles) of benzhydryl isocyanate in 1 ml. of tetrahydrofuran. The mixture is allowed to warm to room temperature and then stirred overnight. The solvent is then removed in vacuo and crystallization affords the desired product, 3-[N-(diphenylmethyl)carbamoyloxymethyl]-7-(2-phenylacetamido)-3-cephem-4-carboxylic acid.

500 mg. of the product is mixed with 1 ml. of anisole and cooled to 0° C. Then 5 ml. of trifluoroacetic acid are added and the resulting mixture is maintained at 0°–5° C. for 12 minutes. The trifluoroacetic acid is removed in high vacuum and when all of the acid is removed, 1 ml. of anisole is added, and the mixture is heated to 30° C. under reduced pressure until all volatile products are removed. The residue is then dissolved in a small amount of aqueous sodium bicarbonate and extracted with ethyl acetate. The aqueous solution is acidified with phosphoric acid to pH 2.5 and extracted into ethyl acetate. The organic solution is dried over anhydrous sodium sulfate and evaporated to afford 3-carbamoyloxymethyl-7-(2-phenylacetamido)-3-cephem-4-carboxylic acid.

EXAMPLE 15

Following the procedures described in Example 5A above, o-nitrobenzyloxycarbonyl isocyanate is reacted with 3-hydroxymethyl-7-(2-thianaphthene-2-acetamido)-3-cephem-4-carboxylic acid to obtain 3-[N-(o-nitrobenzyloxycarbonyl)-carbamoyloxymethyl]-7-(2-thianaphthene-2-acetamido)-3-cephem-4-carboxylic acid.

The 3-[N-(o-nitrobenzyloxycarbonyl)carbamoyloxymethyl] compound so obtained is dissolved in 10 to 20 volumes of dimethoxyethane, pH 5 phosphate buffer is added and the solution is irradiated in a Pyrex flask from 1 to 24 hours with a UV lamp. The resulting solutions are then partitioned between a pH 7.5 buffer and ethyl acetate. The aqueous solution is made acidic to pH 2.5 with phosphoric acid and extracted with ethyl acetate which, after drying with sodium sulfate and concentration, affords 3-carbamoyloxymethyl-7-(2-thianaphthene-2-acetamido)-3-cephem-4-carboxylic acid.

The starting material of this example is prepared by treating the corresponding cephalosporanate with citrus esterase following the procedures described in Example 12B above. The cephalosporanate compound is prepared as described in the pending U.S. application of Christensen et al., U.S. Ser. No. 149,364 filed June 2, 1971.

In the same way other 7-substituted cephalosporanic acids described in said application and other 3-hydroxymethyl-7-acylamido-3-cephem-4-carboxylic acids known in the art are converted to the corresponding 3-carbamoyloxymethyl cephalosporin compounds using the above-described processes.

We claim:

1. A cephalosporin compound of the formula:

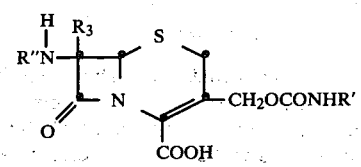

wherein $R_3$ methoxy, R' is benzhydryl or trifluoroacetyl; and R" is 2-thienylacetyl.

* * * * *